United States Patent

Coquard et al.

[11] 4,032,993
[45] July 5, 1977

[54] BIORESORBABLE SURGICAL ARTICLES

[75] Inventors: Jean Coquard, Grezieu-La Varenne; Pierre Sédivy, Sceaux; Michel Ruaud, Ternay; Jean Verrier, Boulogne-sur-Seine, all of France

[73] Assignee: Rhone-Poulenc Industries, Paris, France

[22] Filed: June 25, 1975

[21] Appl. No.: 590,284

[30] Foreign Application Priority Data

June 28, 1974 France .................... 74.22587

[52] U.S. Cl. .................... 3/1; 3/1.4; 3/1.5; 128/92 B; 128/92 C; 128/334 R; 128/335.5; 260/78 A
[51] Int. Cl.² .................... A61F 1/24; A61F 1/00; A61L 17/00
[58] Field of Search .......... 3/1, 1.4, 1.5, 1.9–1.913; 128/92 R, 92 B, 92 C, 92 CA, 92 D, 92 G, 334 R, 334 C, 335, 335.5; 260/75 R, 78 A

[56] References Cited

UNITED STATES PATENTS

| 2,071,250 | 2/1937 | Carothers | 260/78 A |
| 3,463,158 | 8/1969 | Schmitt et al. | 128/334 R |
| 3,620,218 | 11/1971 | Schmitt et al. | 128/334 R |
| 3,773,737 | 11/1973 | Goodman et al. | 128/335.5 X |
| 3,883,901 | 5/1975 | Conquard et al. | 3/1 |

*Primary Examiner*—Ronald L. Frinks
*Attorney, Agent, or Firm*—Cushman, Darby & Cushman

[57] ABSTRACT

Implantable surgical articles are provided which are at least partially bioresorbable and which consist at least partially of a copolyester of succinic acid and oxalic acid possessing receiving units of the general formulae:

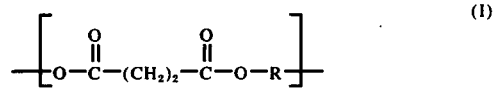

(I)

and

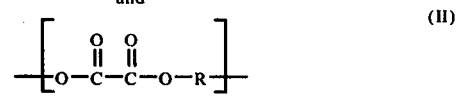

(II)

in which each R radical in the chain, which may be identical or different, represents a linear or branched alkylene radical possessing 2 to 6 carbon atoms, at least 2 of which carbon atoms form part of the polymer chain, a cyclo-alkylene radical possessing 5 to 8 carbon atoms, or a radical of the general formula:

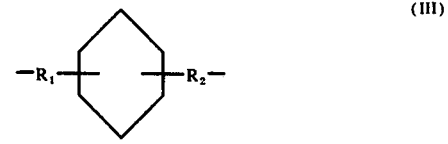

(III)

in which each of $R_1$ and $R_2$, which may be identical or different, represents a methylene or ethylene radical. They are particularly suitable as sutures.

30 Claims, No Drawings

BIORESORBABLE SURGICAL ARTICLES

The present invention relates to bioresorbable surgical articles, especially sutures, ligatures and implantable devices.

Elements for sutures and ligatures and other surgical articles which are partially or completely bioresorbable have been described in French Patent Application No. 2,208,687; these consist of polyesters of succinic acid. Despite the advantages which they possess over catgut or polyesters such as polyglycolides or polylactides, these polyesters possess a relatively slow bioresorbability.

It is known, furthermore, that it is important for the surgeon to have at his disposal various materials which provide him with a wide range of bioresorption properties. In fact, the duration of the resorption process varies with the nature of the wound and with the nature of the tissues involved in the cicatrisation process; it also varies from one individual to another and with the nature of the operation in the case of prostheses. The development of new materials which can be bioresorbed more rapidly thus increases the possible choices available to the surgeon.

Surgical articles which can be used in human or animal surgery and which are completely or partially bioresorbable have now been found, according to the present invention. These consists wholly or partially of a bioresorbable material consisting of a copolyester of succinic acid and oxalic acid possessing chains of units of the general formulae:

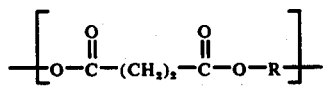
(I)

and

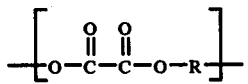
(II)

in which the successive radicals R of the chain, which may be identical or different, each represents a linear or branched alkylene radical possessing 2 to 6 carbon atoms, at least 2 of which are in series between the free valencies, a cycloalkylene radical possessing 5 to 8 carbon atoms, or a radical of the general formula:

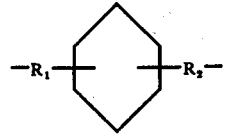
(III)

in which each of $R_1$ and $R_2$, which may be identical or different, represents a methylene or ethylene radical.

More specifically, R can be, for example, an ethylene, methyl-ethylene, 1,2-dimethyl-ethylene, trimethylene, 1-methyl-trimethylene, 2-methyl-trimethylene, 2,2-dimethyl-trimethylene, tetramethylene, pentamethylene, hexamethylene, cyclopentylene, cyclohexylene, 1,3-dimethylene cyclohexyl or 1,4-dimethylene-cyclohexyl radical.

The copolyesters according to the invention advantageously consist of 80 to 99 mol % of units of formula (I) and 20 to 1 mol % of units of formula (II), in a statistical or sequential arrangement.

Ethylene glycol, propylene glycol, propane-1,3-diol, 2-methyl-propane-1,3-diol, 2,2-dimethyl-propane-1,3-diol, butane-1,4-diol, butane-1,3-diol, butane-2,3-diol, pentane-1,5-diol, hexane-1,6-diol, 1,3-dihydroxy-cyclohexane, 1,4-dihydroxy-cyclohexane, 1,3-bis-(hydroxymethyl)-cyclohexane and 1,4-bis-(hydroxymethyl)-cyclohexane may be mentioned as diols which can be used to prepare the copolyesters. These various glycols can be used individually or as a mixture with one another. It is thus possible to employ mixtures comprising 1 to 99 mol % of ethylene glycol and 99 to 1 mol % of one or more other glycols such as 2-methyl-propane-1,3-diol and 2,2-dimethyl-propane-1,3-diol, for example.

The molecular weight of the copolyesters used to produce the surgical articles according to the present invention can vary within very wide limits. However, it must be sufficiently high to enable the polymer to be converted into orientable yarns and films. The upper limit is not critical, provided that the product can be processed by te customary moulding or shaping techniques. The reduced viscosity of the product, in the form of a 2% solution in chlorophenol at 25° C, should generally be at least 50 cm³/g.

The bioresorbable character of polysuccinate homopolymers has been demonstrated in the application mentioned above. If mixtures of this polymer with an oxalic acid polyester are produced, it is found that they still possess a bioresorbable character but articles produced with such mixtures very rapidly lose their mechanical properties. Such a disadvantage can be avoided by the use of copolyesters according to this invention.

It has been found that, in addition to their bioresorbable character, the copolyesters are particularly well tolerated by the tissues in which they are implanted; thus, no inflammatory reaction has been observed in rats after yarns of the copolyester have been implanted for a long period. Moreover, they possess excellent mechanical properties such as tensile strength, tensile strength on the knots and dimensional stability, and are insensitive to moisture and this makes them particularly suitable for the manufacture of surgical articles, especially elements for sutures. The yarns can be handled easily and do not require the use of special means of storage.

Polyesters formed from units of formula (I) or (II) as well as copolyesters containing both these units are products which have been known for a very long time [see U.S. Pat. No. 2,071,250; V. V. KORSHAK and S. V. VINOGRADOVA, "Polyesters", edigted by PERGAMON PRESS Ltd. (1965), pages 31 to 46; H. BATZER et al., Makromolek. Chem., 15, 211 (1955); and V. V. KORSHAK et al., Zh. Obchtch. Khim., 26, 539 (1956)]. They can be prepared by the usual polycondensation processes such as those described by V. V. KORSHAK and S. V. VINOGRADOVA (loc. cit.) or by HOUBEN WEYL, "Methoden der organischen Chemie - Makromolekulare Stoffe", volume 14/2, pages 1 to 29. In order to prepare the copolyesters it is possible, for example, to polycondense, in bulk or in an inert organic diluent, the glycols with the free acids or their dimethyl esters in the presence of customary esterficiation or transesterification catalysts such as sulphuric acid or p-toluenesulphonic acid, metal salts or oxides such as calcium oxide, stontrium oxide, zinc oxide, aluminum oxide, bismuth oxide, iron oxide, titanium oxide, lead oxide, antimony oxide or cobalt oxide, and calcium chloride, zinc acetate or zinc borate. However, because of the low heat stabilities of some acids such as oxalic acid and some diols such as butane-1,4-diol under the usual conditions for bulk polycondensation in vacuo, it can be preferred to carry out the reaction azeotropically in the presence of a solvent which does not give an azeotrope with the diols employed. The procedure used is then in accordance with the method described in "Die Makromoleculare Chemie", (7), 1951, 83–103, H. BATLER, H. HOCTSCHMITT, F. WILOTH and B. MOHR.

The copolyesters can be used for the manufacture of a wide variety of different surgical articles, such as those described in "Handbook of Biomedical Plastics", 1971, H. LEE and K. NEVILLE, Pasadena Technology Press. They are particularly suitable for the manufacture of elements for surgical structures and ligatures, especially in the forms of twisted or untwisted filaments, tapes, bristles, slivers or spun yarns. Use can be made of simple, twisted, corded, combined, texturized or wrapped yarns; these various terms are used in accordance with the definition which is given for them in French Standard Specification NF G 00-005. These various elements for sutures can consist wholly or partially of the bioresorbable copolyesters. thus it is possible to use a filament made of copolyester or a filament comprising a core made of a non-resorbable synthetic material such as polyethylene glycol terephthalate, polyamide or polypropylene, and an outer covering made of copolyester. It is also possible to use a composite element consisting of a yarn made of natural (such as linen or silk) or synthetic material covered with a copolyester, or a yarn of variable structure comprising bioresorbable filaments and non-resorbable filaments.

Amongst the other surgical articles for which the specified copolyesters can be used, there may be mentioned knitted fabrics comprising resorbable yarns and optionally non-resorbable yarns or non-resorbable yarns covered with a layer of copolyester; non-wovern fabrics prepared from non-bioresorbable fibers and a resorbable binder; and sheets made of non-resorbable materials covered on one or both faces with a copolyester. The completely or partially resorbable knitted and woven fabrics can be used in the form of sheaths intended to facilitate the implantation of various prostheses such as that described in French Pat. Nos. 2,031,699 and 2,071,172 for the correction of valvular diseases and especially diseases of the mitral valve; pipelines for removing biological liquids (in particular, artificial ureters) described in French Pat. No. 2,133,083; and vascular prostheses such as those described in French Pat. No. 2,122,032.

The copolymers are also very suitable for the manufacture of surgical articles such as tubes of various shapes, for example "Y"-shaped tubes and "T"-shaped tubes, bars, plates, rings and screws intended to be implanted temporarily or permanently. Partially or completely bioresorbable tubular prostheses have been described in U.S. Pat. Nos. 2,127,903, 3,272,204, 3,304,557, 3,316,557 and 3,479,670 to which reference should be made for further details.

The copolyesters for the manufacture of surgical articles can be shaped in the usual manner. Thus, filaments, tapes or sheets can be prepared by extrusion of the polymer in the molten state, followed by stretching at a ratio sufficient to cause the orientation of the polymer chains, and fixing the article thus obtained.

The copolyesters can contain various adjuvants such as fillers, dyestuffs and plasticizers which are chemically inert and do not cause reactions on the part of living tissues, these various adjuvants being themselves preferably resorbable.

They can be used individually or in the form of a mixture with materials which are non-bioresorbable or more or less resorbable than themselves, for example, respectively, polyesters of the polyethylene glycol terephthalate of polyethylene glycol adipate type, or of the polylactide or polyglycolide type.

The surgical articles according to this invention can be sterilized easily by means of the techniques usually employed in surgery, for example by radiation treatment.

The following Example further illustrates the present invention.

EXAMPLE

Preparation and shaping of the copolycondensate 159.42 g of succinic acid, 13.78 g of oxalic acid, 136.53 g of butane-1,4-diol, 3 g of p-toluenesulphonic acid and 1,200 cm$^3$ of toluene are introduced into a 1 liter 3-necked flask equipped with a stirring system and a reflux condenser with a Florentine separator. The mixture is heated under reflux for 1 hour 30 minutes so as to effect esterification of the oxalic and succinic acids, removing the water of the reaction by azeotropic distillation followed by decanting. The separator is then replaced by a Soxhlet apparatus packed with a 4 Angstrom dehydrating molecular sieve. The reaction mixture, which is kept under reflux, becomes increasingly viscous. After refluxing for 42 hours, the mass obtained is poured, with stirring, into 5 l of methanol. The fibrous white polymer obtained is filtered off, washed with 3.5 l of methanol, filtered off and then dried at ambient temperature in vacuo.

232 g of polymer are obtained, corresponding to a 90% yield.

The reduced viscosity of the product, in the form of a solution in chlorophenol of concentration 2 g/l at 25° C, is 164 cm$^3$/g.

The copolyester is purified by dissolving it in 1,200 cm$^3$ of methylene chloride and then precipitating it by pouring into 5 l of methanol; after drying in vacuo at ambient temperature, the copolyester has a reduced viscosity of 159 cm$^3$/g. Its melting point is 105° C and it is stable to heat under nitrogen up to 250° C.

Filaments of gauge 15 decitex are prepared from the above copolyester by melt spinning at 105° C followed by stretching on a plate at 77° C in a ratio of 6.5:1. These filaments possess the following mechanical properties (determined according to Standard Specification NF G 07,008, April 1961):

Tensile strength: 2.5 g/decitex,
Elongation at break: 49% and
Tensile strength at a knot: 2.2 g/decitex.

2. Determination of the local tolerance of implants in rats

A stretched monofilament of diameter 300 to 400 $\mu$ is produced using the copolyester prepared as described above and is sterilized by immersion for 1 hour in 70° GL (Gay-Lussac) strength ethyl alcohol.

1 cm long samples are implanted, by means of a semi-curved needle, rats (caesarean originated, barrier sustained) weighing 250 to 350 g; the implantation is carried out, on the one hand, in the paravertebral muscles and, on the other hand, under the skin of one of the sides of each animal. Four rats (two male and two female) each receive the two implants. Two months after the implantation, the animals are killed and the muscular implantation zone (implant and paravertebral muscular mass) and the subcutaneous implantation zone (skin, implant and underlying portion of muscle) are removed in each case. The following examinations are carried out on each sample removed:

a. Macroscopic examination after transverse section of one of the ends of the muscular mass (intramuscular implant) or detachment of the skin at one end (subcutaneous implant) of each sample.

b. Histological examination after fixing the samples in BOUIN liquid, inclusion in paraffin, cutting to 5 $\mu$ thickness and colouration using hematein/phloxine/saffron. The following results were obtained:

a. Macroscopic examination

Two months after the implantation, no tissue reaction which could be detected macroscopically was observed either with respect to the muscle or with respect to the subcutaneous tissue.

b. Histological examination
Reaction of the tissue

This reaction is restricted to a very discrete fibrous sheath around the implant and to the presence of a few multinucleate giant macrophage and histiocyte cells situated in contact with the implant itself.

No change which could relate to a possible toxic effect of the material was detected on the sections.

In short, the local tolerance in rats is very good from the macroscopic point of view and from the histological point of view.

3. Determination of the bioresorbability "in vitro"

The bioresorbability of the copolyester obtained above is determined by measuring the variation in the reduced viscosity of a sample or polymer which is in the form of flakes and is incubated for varying periods of time is an enzyme extract. The test was carried out in the following way:

a. Preparation of the enzyme extract

"Fauves de Bourgogne" rabbits, of approximately 2.5 kg, are killed by means of chloroform. The muscles from the back and the thighs are removed and frozen at −20° C. They are then ground rapidly in a mincer. 300 g of ground product are dispersed in 500 ml of 0.2 M citrate buffer of pH 4.1 which has been cooled beforehand to +2°. The suspension obtained is again ground for 1 minute (twice; grinder rotating at 2,000 revolutions/minute), with external cooling (mixture of ice and salt at approximately −13° C) so as to keep the temperature of the homogenized product below +10° C during the operation.

The homogenized product then undergoes an ultrasonic treatment (frequency: 20 kHz) for 2 minutes, taking the same cooling precautions. It is then centrifuged at 6,500 kilogals, at 0° for 20 minutes. The supernatant liquid, filtered through glass wool, forms the enzyme extract; its pH is approximately 4.5.

b. Reaction between the copolyester to be investigated and the enzyme extract

A 100 mg sample of the copolyester to be investigated is incubated at 37° C, with agitation (shaking table rotating at 80 revolutions/minute), in the following reaction medium:

| Enzyme extract | 40 ml |
| Streptomycin sulphate | 2 mg |
| Sodium salt of penicillin G | 2 mg |
| Sodium nitride | 8 mg |

This reaction medium is renewed every day; during each renewal process, the samples are washed carefully with distilled water.

In parallel, other 100 mg samples of the product to be investigated are incubated in reaction media in which the enzyme extract is replaced by 0.2 M citrate buffer of pH 4.5.

The product to be investigated, which is in the form of flakes, is enclosed in a gauze bag for incubation purposes.

c. Examination of the copolyester after reaction

After 160 hours of incubation, the samples of the product to be investigated are recovered, washed several times with distilled water, drained on filter paper and dried under reduced pressure at 50° C.

The reduced specific viscosity of solutions of the product in 2-chloro-phenol at 25° C is then determined, as is that of the product before incubation.

The following results were obatined:

| Nature of the incubation medium | Reduced specific viscosity |
| --- | --- |
| None | 143 |
| Citrate buffer | 130 |
| Enzyme extract | 114 |

It is found under these conditions that incubation in the active enzyme extract results in considerable degradation of the copolyester.

d. Reaction between a copolyester yarn and the enzyme extract

The experiment described in paragraph (b) is repeated, but is carried out on calibrated yarns as described in paragraph 2.

e. Examination of the copolyester after reaction

After 5 or 12 days of incubation, the samples of yarns are recovered, washed several times with distilled water, drained on filter paper and dried under reduced pressure at 50° C.

The reduced specific viscosity of solutions of the product in 2-chloro-phenol at 25° C is then determined.

The following results are obtained:

| Nature of the incubation | Reduced viscosity after incubation for 5 days | Reduced viscosity after incubation for 12 days |
| --- | --- | --- |
| Citrate buffer | 134 | 109 |
| Enzyme extract | 131 | 104 |

The reduced viscosity of the control is 143.

f. Examination of the yarns after reaction

The breaking force of the yarns is measured on a tensometer of the Richard type.

The following results, expressed in grams, are obtained.

| Nature of the incubation | Incubation for 5 days | Incubation for 12 days |
|---|---|---|
| Citrate buffer | 537 | 423 |
| Enzyme extract | 476 | 430 |

A control has a tensile strength of 513 g.

We claim:

1. A sterile implantable surgical article which is at least partially bioresorbable, and which consists at least partially of a copolyester of succinic acid and oxalic acid possessing recurring units of the general formulae:

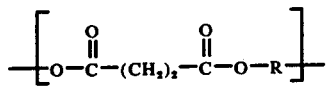  (I)

and

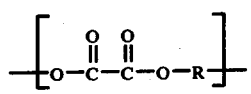  (II)

in which each R radical in the chain, which may be identical or different, represents a linear or branched alkylene radical possessing 2 to 6 carbon atoms, at least 2 of which carbon atoms form part of the polymer chain, a cyclo-alkylene radical possessing 5 to 8 carbon atoms, or a radical of the general formula:

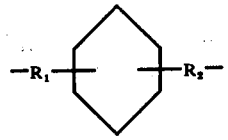  (III)

in which each of $R_1$ and $R_2$, which may be identical or different, represents a methylene or ethylene radical.

2. A surgical article according to claim 1, in which tthe copolyester has a reduced viscosity at least 50 cm³/g as a 2% by weight solution in chlorophenol at 25° C.

3. A surgical article according to claim 1, in which the copolyester consists of 1 to 20 mol % of units of formula (II) and 99 to 80% of units of formula (I).

4. A surgical article according to claim 1, which is in the form of a suture.

5. A surgical article according to claim 4, which is in the form of a filament.

6. A surgical article according to claim 1, which is in the form of a prosthesis for replacing supporting or assisting in the repair of human of animal organ.

7. A surgical article according to claim 6, which is inthe form of a solid-walled tube.

8. A surgical article according to claim 6, which is in the form of a woven, textile web.

9. A surgical article according to claim 1, in which the copolyester is present as a coating over a core of non-bioresorbable material.

10. A surgical article according to claim 9, in which the non-bioresorbable material is selected from the group consisting of polyethylene glycol terephthalate, polyamide and polypropylene.

11. A surgical article according to claim 1, in which the copolyester is combined with another material which is bioresorbable.

12. A surgical article according to claim 11, in which the other material is selected from the group consisting of a polylactide and a polyglycolide.

13. In a method of repairing or replacing a part of the body of a human or non-human animal the improvement wherein a surgical article as defined in claim 1 is incorporated either temporarily or permanently.

14. A surgical article according to claim 1 which is in the form of a bristle.

15. A surgical article according to claim 1 which is in the form of a yarn.

16. A surgical article according to claim 1 which is in the form of a tape.

17. A surgical article according to claim 1 which is in the form of a sliver.

18. A surgical article according to claim 6 which is in the form of a bar.

19. A surgical article according to claim 6 which is in the form of a plate.

20. A surgical article according to claim 6 which in the form of a screw.

21. A surgical article according to claim 6 which in the form of a ring.

22. A surgical article according to claim 6 in the form of a knitted tube.

23. A surgical article according to claim 6, in the form of a knitted textile web.

24. A surgical article according to claim 6, in the form of a non-woven textile web.

25. A surgical article according to claim 1 in the form of a twisted yarn.

26. A surgical article according to claim 1 in the form of a corded yarn.

27. A surgical article according to claim 1 in the form of a combined yarn.

28. A surgical article according to claim 1 in the form of a texturized yarn.

29. A surgical article according to claim 1 in the form of a wrapped yarn.

30. A surgical article according to claim 1 in the form of a spun yarn.

* * * * *